United States Patent
Campbell et al.

(10) Patent No.: US 11,935,633 B1
(45) Date of Patent: Mar. 19, 2024

(54) SECURE MOBILE DEVICE PROVISIONING SYSTEM

(71) Applicant: Epic Systems Corporation, Verona, WI (US)

(72) Inventors: Janet L. Campbell, Madison, WI (US); Michael R. Epley, Madison, WI (US); Dustin Gage, Madison, WI (US); Brian Weisberger, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 1261 days.

(21) Appl. No.: 14/523,442

(22) Filed: Oct. 24, 2014

Related U.S. Application Data

(60) Provisional application No. 61/895,753, filed on Oct. 25, 2013.

(51) Int. Cl.
*G16H 10/60* (2018.01)
*H04L 9/40* (2022.01)

(52) U.S. Cl.
CPC ............. *G16H 10/60* (2018.01); *H04L 63/08* (2013.01)

(58) Field of Classification Search
CPC ........ G06F 19/322; H04L 63/08; G16H 10/60
See application file for complete search history.

(56) References Cited

U.S. PATENT DOCUMENTS

| | | | | |
|---|---|---|---|---|
| 2013/0145420 A1* | 6/2013 | Ting | ................ | H04L 63/08 726/1 |
| 2013/0219516 A1* | 8/2013 | Shimshoni | ............ | H04L 63/083 726/28 |
| 2013/0263211 A1* | 10/2013 | Neuman | ................. | H04L 63/08 726/1 |
| 2014/0095207 A1* | 4/2014 | Dhir | ........................ | G06F 19/00 705/3 |
| 2014/0197232 A1* | 7/2014 | Birkler | .................. | G06F 21/313 235/375 |
| 2014/0351589 A1* | 11/2014 | Chenna | ............... | H04L 63/0823 713/168 |

\* cited by examiner

*Primary Examiner* — Gregory D. Moseley
(74) *Attorney, Agent, or Firm* — Boyle Fredrickson, S.C.

(57) ABSTRACT

The present invention relates to a system method of provisioning mobile device security settings to provide authorized users with secure access. The system and method uses a generated, computer-readable authentication code that is read by a mobile device. The authentication code enables an unprovisional mobile device to request security credentials to enable a user of the mobile device to connect to a secured system.

6 Claims, 5 Drawing Sheets

SECURE MOBILE DEVICE PROVISIONING SYSTEM

CROSS-REFERENCE TO RELATED APPLICATIONS

This application claims the benefit of U.S. Provisional Application No. 61/895,753, filed Oct. 25, 2013, the entirety of which is hereby incorporated by reference.

STATEMENT REGARDING FEDERALLY SPONSORED RESEARCH OR DEVELOPMENT

Not applicable.

FIELD OF THE INVENTION

The present application relates to systems and methods for "imprinting" a tablet or other mobile device (such as an Apple® or Android® phone) with the information it needs to provide authorized users with secure access to a patient's electronic health record during an active hospital admission.

BACKGROUND OF THE INVENTION

Many modern health care organizations have adopted electronic health record (EHR) systems such as EpicCare, by Epic Systems Corporation. The EHR provides for the systematic collection of electronic health information about individual patients including demographic, medical history, allergies, medication, immunizations, lab results, orders, medical imaging (e.g., radiology), and vitals. EHRs like EpicCare further allow healthcare providers to collect financial and billing information, exchange records with other health care organizations, and generate reports and statistic information concerning the healthcare organization's patient population.

Patient portals are website services offered to provide patients with access to information stored in a health care system's EHR. Patient portals provide patients with access to much of the historical clinical health information (information about past encounters, certain lab results, medication orders, etc.) recorded in the patients record as well as access to a selection of other health care related functions like scheduling, appointment reminders, and secure messaging. Such patient portals are commonly used in outpatient settings from the home or while traveling.

Such patient portals often follow common and known patient sign-up and authentication models used throughout the industry. In one example, a patient registers with their healthcare provider. Their healthcare provider validates their identity either by using identity verification services (such as services offered by Experian®) or by providing the patient with a unique, alphanumeric key mailed to their home. Once the patient's identity has been verified, the patient creates an account (username and password) and is able to log into the patient portal.

Epic Systems Corporation recently introduced a tablet-based application that gives an admitted patient (or, in some cases, the patient's family, proxy, guardians, or visitors) more information about the patient's current stay in the hospital. This application provides the patient real-time information about their stay and their health (e.g., blood pressure, pulse, and other vitals) as well as access to patient education information concerning their stay. The application also provides the patient information about their care team and may provide access to other room-related functions: ordering meals, changing the television, adjusting the bed, etc. This application can strengthen the clinician-patient bond while making the patient's hospital stay more enjoyable and productive. While focusing specifically on a patient's hospital stay, MyChart Bedside can engage a patient to continue his active partnership with his healthcare providers by using other electronic patient portals upon discharge. MyChart Bedside can also serve as a way to introduce admitted patients to other patient services, including personal health records and patient portals, if they aren't yet familiar with it so that they can use such services to remain engaged in their case after leaving the hospital.

If every patient (or proxy) must create a new account to use an inpatient patient application, the ordinary account creation process would be cumbersome. Patients for a limited stay might be discouraged from using the application. Patients may be too distracted or consumed with other medical concerns to create an application. Further, if devices running the inpatient application are shared among patients, then re-provisioning the device repeatedly may be time consuming and error prone. And it is anticipated that a patient or a patient's family, friends, proxies or guardians may have their own portable devices which may be used to access the patient's records. It is further anticipated that more than one device might be used by a patient and the patient's proxies in one room and that the devices may be shared.

In addition to inpatient mobile applications directed at patients, there exist a number of applications directed at caregivers, clinicians, providers, and other EHR users including Haiku® and Canto® from Epic Systems Corporation. While generally the devices are personal and continuously used by a single provider, it is envisioned that a fleet of tablets might be available for use by any EHR user.

Accordingly, in both cases there is a need for a better way to provision devices by "imprinting" the device with information needed to provide authorized users with secure access to a secure system, including a patient electronic health record, the health record system itself, or other similar system.

BRIEF SUMMARY OF THE INVENTION

One embodiment of the present invention provides for a system and method of provisioning a mobile device to a user. In one embodiment, an EHR creates a computer-readable code (such as a QR code or similar bar code) with enough information to uniquely identify a tablet user or list of users. In one embodiment, this information may include a client token. The client token may be a unique identifier such as an UUID or unique, base64 encoded identifier. In yet another embodiment, the computer-readable code might use near-field communications or RFID technology such that a device used by a nurse, clinician or other hospital worker can communicate with the mobile device.

In addition to the client token, the computer-readable code may contain appropriate information selected from the group of: organization information, patient information (e.g., patient identifier), admission information (e.g., encounter identifier), and a list of authorized users (user identifiers). In some embodiments, the computer-readable code may expire after a period of time.

In some embodiments, the computer-readable code may be printed for delivery to a patient such as on an instruction sheet. In other embodiments, the computer-readable code may be displayed on another screen (such as a nurse's mobile device, workstation, or large screen in a patient's room).

In some embodiments, the user then uses the unauthenticated application to scan the computer-readable code. In some embodiments, the unauthenticated application shows only a "welcome" or similar "home" screen with instructions to scan a computer-readable code. In some embodiments, the scan be performed using a built-in camera or other optical device associated or affixed to the device.

Using the information obtained from the computer-readable code, in some embodiments, the application may query a centralized address book using an organization identifier in order to retrieve an organization's server address or may, alternatively, attempt to use the last known server address before querying the centralized address book. In other embodiments, the computer-readable code may contain sufficient information to determine the organization's server address. In yet other embodiments, the application itself may have the organization's server address. In yet other embodiments, the organization's server address might be determinable by other information such location of the device (e.g., GPS information), public or private wireless networking functionality, or other indicators such as RFID tags located at or near the patient bed.

In some embodiments, once the organizations server has been determined, the application transmits the other identifying information to the server to establish a link. Such identifying information may be one or more of the following: the patient identifier or the encounter identifier.

BRIEF DESCRIPTION OF THE SEVERAL VIEW OF THE DRAWINGS

DETAILED DESCRIPTION OF THE INVENTION

Generally, the present invention is directed at a system and method for provisioning a mobile device (or fleet of mobile devices) with information needed to provide authorized users with secure access to a remote system such as an EHR. It will be appreciated that while the provisioning process is described with specific reference to a patient accessing his or her own medical record, the provisioning process could be used in any number of possible systems where secure access from a mobile device is sought.

Figure 1:
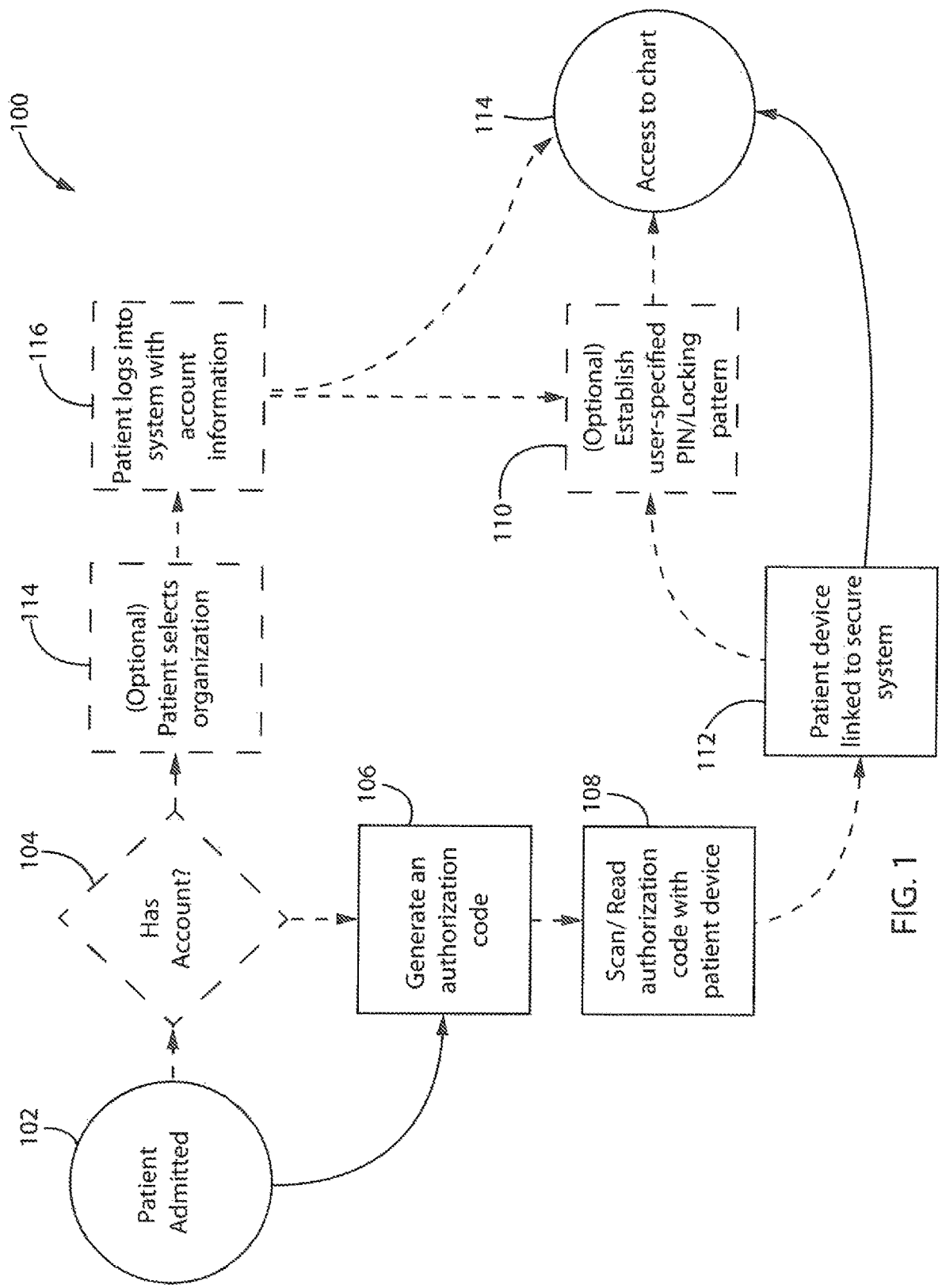
FIG. 1 is an exemplary flowchart of the provisioning process for a patient device in one embodiment of the present invention.

FIG. 1 is an exemplary flowchart of one possible embodiment of provisioning process 100 for a patient device of the present invention. Provisioning process 100 starts with a patient being admitted to a healthcare system at step 102. At step 102, a patient is admitted, assigned a room and a care team. In addition, a patient may be provided a tablet, mobile device, or another specific device associated with the patient's room. In addition, the device might be the patient's own device brought from outside the hospital. In addition, the process is also applicable to non-patient devices, such as devices owned or provided to the family members, visitors, proxies, or guardians of the patient authorized to have access to some or all of the patient's records. For simplicity of this example, we will generically describe this as the patient device.

The patient device will require the secure application of the system. In the case the patient device is provided by the healthcare provider or is associated with the room, then the patient device will have the application installed. In the case it is a patient-owned or patient-supplied device, then the patient will be required to download the application. In one embodiment, the application is available for download from a publicly available application store such as the Google Play market or Apple iTunes store. In other embodiments, the application may be available from a healthcare provider's own internal servers.

Figure 2A:
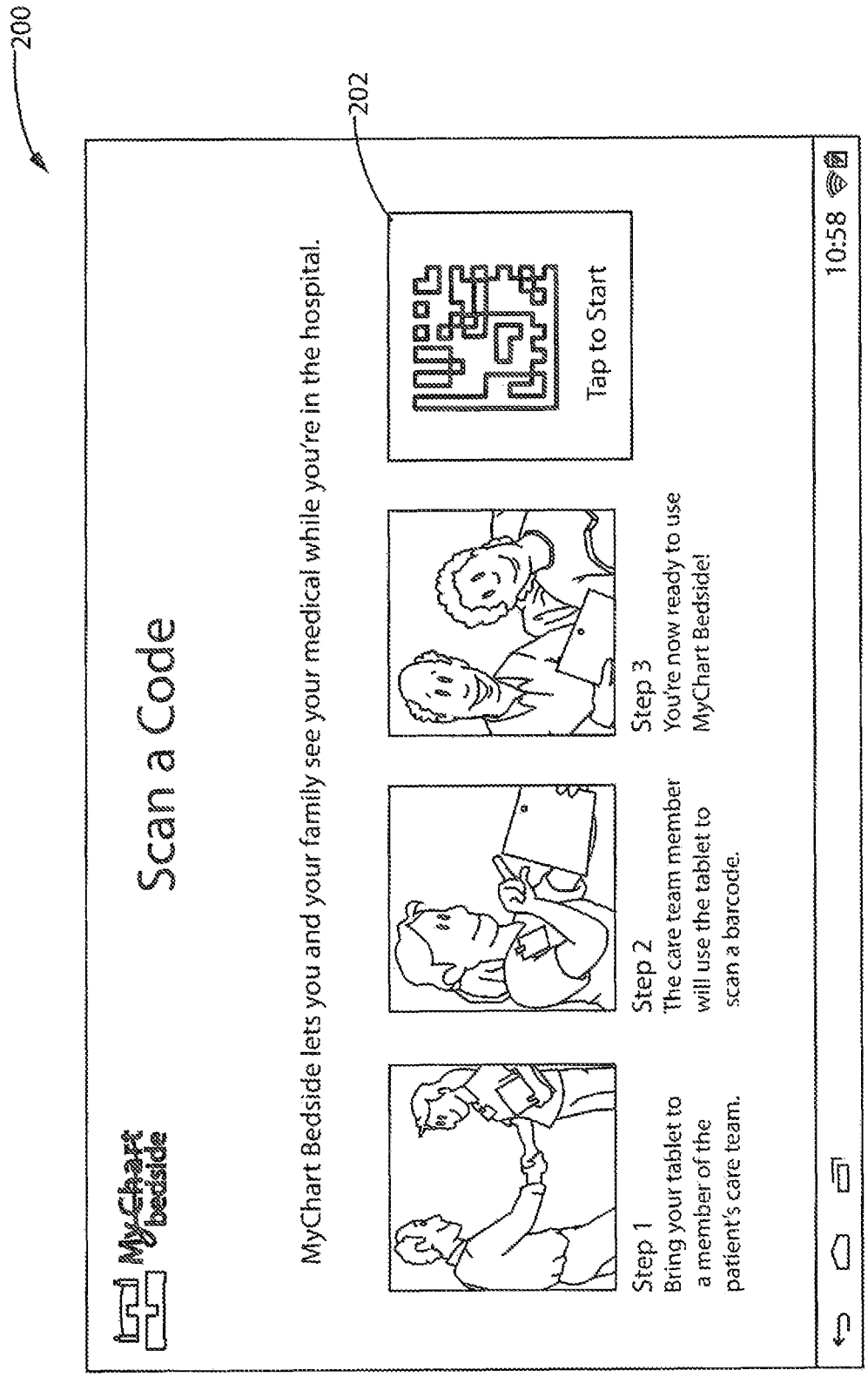
FIG. 2A is an exemplary home screen for an application prior to provisioning in accordance with one embodiment of the invention.

At step 102, a patient device running the secure application is in an non-provisioned state. An example screenshot of the secure application is shown in FIG. 2A. The welcome screen 200 includes basic instructions for provisioning establishing a secure connection to the patient record. The welcome screen 200 also includes a button 202 that enables the reading or scanning functionality used in step 108, discussed below. In embodiments of the invention that do not include scanning or reading a bar code (such as using near-field communication, Bluetooth communication, or ad hoc wireless networking), button 108 may be excluded or may be replaced with a button that sets the device in a listen mode (or broadcast mode depending on implementation) awaiting receipt of the computer-readable authorization code.

In the example process, once a patient has been admitted and has a patient device with the secure application, the process can proceed to option decision 104. It is anticipated that some patients (or their family members, visitors, proxies, or guardians) may already have access to the healthcare providers' secure system, such as a patient portal. In this case, it is anticipated that the secure application may be able to leverage the existing account infrastructure. If a patient does have such an account, then the process moves to optional step 114. At optional step 114, the secure application may request a patient select his or her healthcare organization. It will be appreciated that if the secure application is a secure application pre-installed by an organization on the patient device, a secure application available from a healthcare organization's internal server, or a secure application that is able to determine the healthcare organization based on the patient device location, this step 114 may be performed automatically by the secure application. Proceeding from optional step 114, provisioning process 100 moves to optional step 116 in which the patient logs into the secure application using his or her account information. Account information may be user name and password. In addition, the account information may additionally include another secondary factor such as fingerprint or other biometric verification, a confirmation code, or secondary validation check such as a personal validation such as a security question. If the patient is successfully logged in, then provisioning process 100 proceeds either to optional step 110, described below, or directly to step 114 described below.

Figure 2B:
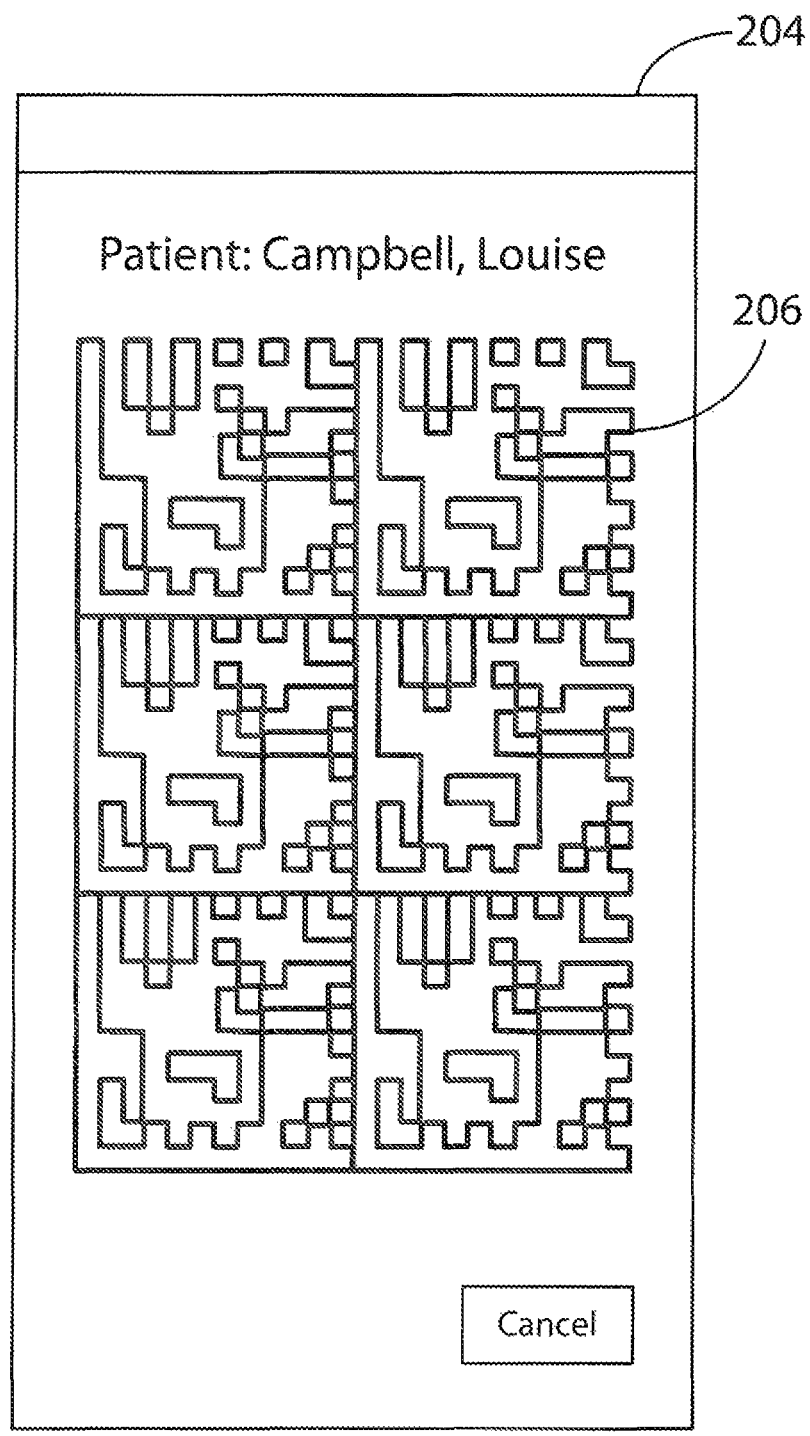
FIG. 2B is an exemplary embodiment of the computer-readable code used in the provisioning process of one embodiment of the present invention.

In embodiments of provisioning process 100 where there is no other patient account or where a patient does not have an account to the secure system, provisioning process proceeds to step 106 in which a computer-readable authorization code is generated by the secure system. FIG. 2B in an example of a QR code, i.e., a 2D barcode, that is suitable for use as a computer-readable authorization code. The process of generating a computer-readable authorization code is discussed in greater detail in the context of FIG. 3 below. The computer-readable authorization code may be "delivered" in a number of possible mediums including printed, displayed on a screen, stored and transmitted via near-field communication techniques, transmitted using Bluetooth or similar communication techniques, transmitted using an ad hoc wireless network, or stored and transmitted in a medium that can be read by the patient device (such as on USB media or via a wireless connection).

Once a computer-readable authorization code is generated by the secure system in provisioning process 100, the computer-readable authorization code is scanned or read by the patient device at step 108. In some embodiments, the computer-readable authorization code is a 2D bar code, such as a QR code. In this embodiment, the patient device reads the computer-readable authorization code using a built-in camera or a barcode reader. The secure application may have built-in functionality to read the barcode or may rely on third party applications or camera functions to do so. In an alternative embodiment, as mentioned above, the computer-readable authorization code may be shared with the patient device using near-field communication techniques. A nurse's or clinician's or other secure system user's device can transport the code to the patient's room where it can then be communicated to the patient device. Examples of such techniques might include NFC related communications, ad hoc wireless communication between devices, or known syncing techniques.

Once the patient device reads or scans the computer-readable authorization code, the provisioning process 100 continues to step 112. At step 112, the secure application uses the information stored in the computer-readable authorization code in communication with the secure system to associate the patient device with the secure system. The process of linking the patient device is discussed in greater detail in the context of FIG. 3 below. In one embodiment, the computer-readable authorization code contains some basic information to identify to which part of the secure system to associate the patient device. The computer-readable authorization code may also contain server address information at which the secure system is addressable and to which the secure application should communicate or other healthcare organization information. It will be appreciated that in some embodiments of the provisioning process, the organization doing the provisioning may be unknown to the secure application. For example, in the case that the secure application is publicly available for download and not associated with a specific organization, it may be necessary to provide the device information about the organization or the organization's infrastructure to which the patient device is attempting to communicate.

In one embodiment of the present invention, once the computer-readable authorization code is consumed by the patient device and the patient device is linked with the secure system, it is disabled and any future attempts to use the authorization code are logged and treated as unauthorized access for security purposes.

In some embodiments of step 112, the patient device sends other information to the secure system in addition to the computer-readable authorization code including basic device data (e.g., manufacturer, model, operating system, operating system version), patient identifier, and/or location information (GPS information, wireless network information, etc.).

In some embodiments of step 112, the secure system returns information to the secure application. For example, the secure system will generate a server token that will uniquely identify the patient device's authorization at the organization. This server token is a shared secret between the secure system and the secure application. The secure application on a successfully linked patient device can then use the server token when communicating with the secure system. In other embodiments, the secure system and secure application may just use a patient identifier or other record identifier to associate with the linking record.

Once a link is successfully established between the secure application and secure system in step 112, provisioning process proceeds to either optional step 110 or to final step 114. At optional step 110, the user of the patient device is presented with an intermediate screen from which the user selects a user-specific personal identification number, lock pattern, password, passphrase, or similar security feature. The secure application may also request biometric identifier such as a fingerprint or picture of the user to be used as an additional security feature. In some embodiments, the picture of the user may be used for facial recognition purpose or as a profile picture or both.

Figure 4A:
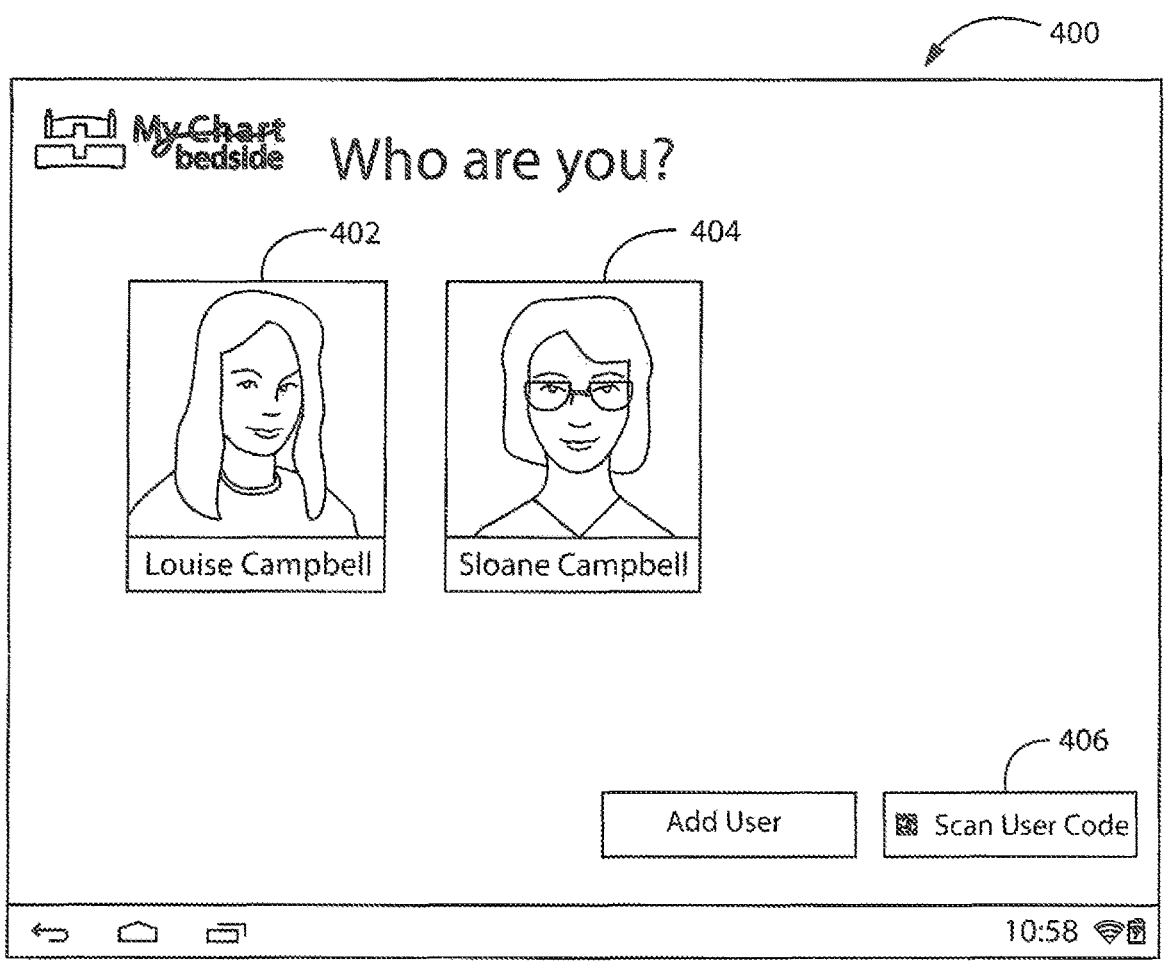
FIG. 4A is an exemplary screenshot for an application on a mobile device in accordance with the present invention following consumption of the computer-readable code.

In some embodiments, step 110 may also include the selection from one of the authorized users when more than one user was authorized for access to the same patient record. An exemplary screenshot of such an interface is shown in FIG. 4A. The user selection screen 400 allows the user of the patient device to select from the one of two authorized users 402 and 404 or scan a new user using a button 406. The secure application then can be used and personalized based on the selected user. For example, if the patient is authorized user 402 and the patient's daughter is authorized user 404, the selection of the patient authorized user 402 in the secure application may present different information and functionality than for the patient's daughter. In this embodiment, it will be appreciated that both authorized users 402 and 404 have access to the same patient record, but may be presented with different sets of functionality and features.

Once optional step 110 is complete, if the particular implementation does not follow optional step 110, provisioning process 100 proceeds to the final step 114. At final step 114, the secure application on the patient device can access the patient information stored on the secure system as well as other features and functionalities enabled by the secure system. In the example of a patient device for use within a healthcare organization, the secure application may allow secure messaging to the patient's clinician, allow the patient to view of upcoming scheduled events, access and view patient education information, view and review the patient's own vital signs, change the television channel, order meals, schedule follow-up visits, review information about the patient's current care team, track patient reported information (discomfort/pain levels), and activate an account on the healthcare organizations personal health record system or patient portal.

Figure 4B:
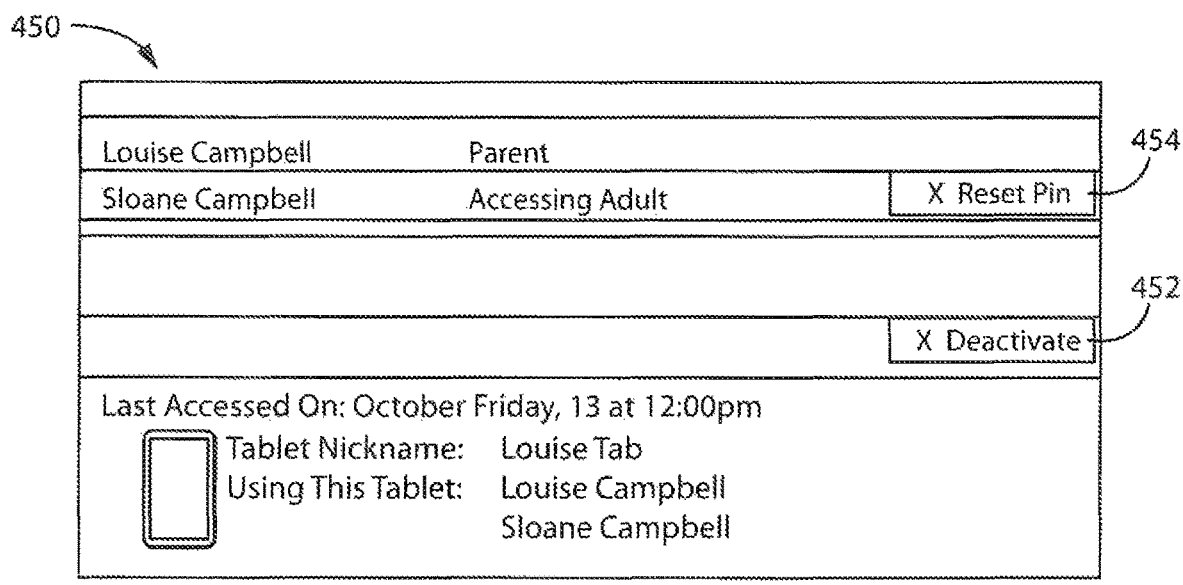
FIG. 4B is an exemplary screenshot for an administrative view of the provisioned tablet as viewable in the electronic health record system.

Not shown in FIG. 1, a patient device can be un-provisioned directly from the device itself or can be un-provisioned at the secure system. In the latter case, if a patient device is lost or stolen, a secure system user can deactivate the link. FIG. 4B in an exemplary screenshot of a secure system administration screen 450. Administration screen 450 shows a record for a provisioned patient device for patient 402. As shown in the screen, the secure system user can reset a pin set at optional step 110 by clicking button 454 or deactivate the provisioned patient device by clicking button 452.

Figure 3:
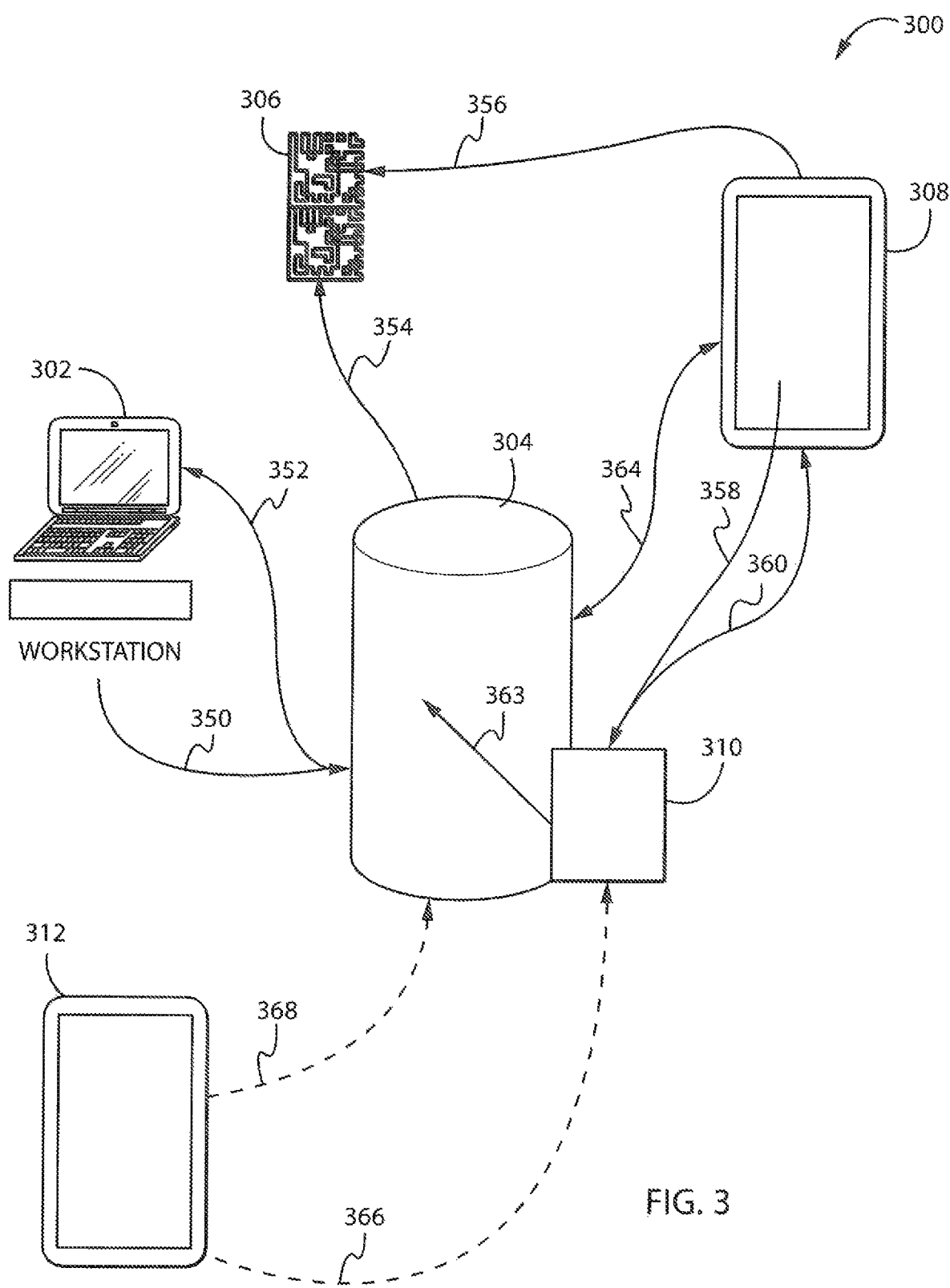
FIG. 3 is one embodiment of a provisioning system in accordance with the present invention.

FIG. 3 is one embodiment of the provisioning system of the present invention. The system comprises a workstation 302, an electronic health record system 304, a patient device 308, and a server 310 in communication with the electronic health record system 304. Electronic health record system 304 comprises patient health records (not shown) as well as programming and software to interact with the data stored in the patient health record system 304.

In this embodiment, a nurse (or other user of the electronic health record system 304) access the workstation 302. Workstation 302 is in communication with electronic health record system 304 as shown by paths 350 and 352. Workstation 302 may be located in any location, including at a nursing station, in the patient room (where the workstation 302 may also be used for normal documentation into the electronic health record system 304). While workstation 302 is shown as a desktop computer, it will be appreciated that workstation 302 might be any number of devices including a tablet, laptop, or other computerized device. The nurse, wanting to provision a patient device, requests the electronic health record along path 350 to generate a computer-readable authorization code. The request will include a patient identifier. The request may also include one or more non-patient authorized users including those listed as proxies in the electronic health record system or other individuals designated by the nurse.

In response, the electronic health record system 304 generates a client token. In one embodiment the client token is a unique, base64 encoded identifier for a device. In this embodiment, the electronic health record system 304 stores the client token together with a patient identifier. The electronic health record system 304 may also store a list of the one or more non-patient authorized users selected or designated by the nurse with the client token. If the electronic health record system 304 time limits the life of any particular client token, the electronic health record system 304 will also store an expiration time.

In addition, the electronic health record system 304 will generate a computer-readable authentication code 306. In the embodiment shown in FIG. 3, the computer-readable authentication code 306 is a 2D barcode, a QR code. The computer-readable authentication code 306 contains at least the client token. In addition, the computer-readable authentication code 306 may contain additional information such as the address of the server 310. In systems in accordance with the present invention where the secure application running on patient device 308 is publicly available (such as from a public app store), the patient device 308 may not know the "address" of server 310 or how to connect to server 310. This address information can be a URI.

In one embodiment, the computer-readable authentication code 306 can return to the workstation 302 via path 352. From workstation 302 the computer-readable authentication code 306 can be displayed on the screen or printed to a local printer. Alternatively, the electronic health record system 304 can send the computer-readable authentication code 306 to a network printer (not shown) to be printed, to a different workstation in the patient room (not shown) for display, to a separate mobile device under the control of the nurse (not shown).

It will be further appreciated that the computer-readable authentication code need not be a QR code. It is anticipated that the computer-readable authentication code could be any form of messaging that would enable to content of the computer-readable authentication code to be communicated to the patient device 308. For instance, the computer-readable authentication code could be communicated using NFC technology. The patient device 308 would "read" the computer-readable authentication code from a transmitting located in the patient's room. This transmitting device might be a workstation in the room (not shown), a specialized NFC adapter in communication with the electronic health record system 304 (not shown), or the nurse's own mobile device.

In any case, the patient device 308 needs to be able to receive the information stored in the computer-readable authentication code 306. In the shown embodiment, the patient device 308 is configured with a digital camera. In this embodiment, from within the secure application running on the patient device 308, the patient device 308 takes a picture of the computer-readable authentication code 306. The patient device 308 interprets the information (e.g., the client token and the address of server 310) stored in the computer-readable authentication code 306. Optionally, the secure application running on the patient device 308 may validate the information. The patient device 308 then transmits a request along path 358 to be identified as an authorized device to server 310 using the address information. The request includes the client token.

Server 310 receives the request together with the client token from the patient device. Server 310 validates the client token with the electronic health record system 304. This validation confirms the validity of the client token, checks that the token has not already been consumed, and, if appropriate or necessary, checks to ensure that the client token has not expired. If the client token does not match a known client token, has been previously consumed, and has expired, then server 310 will return an error message to the patient device 308.

If the client token is valid, then server 310 links the patient device 308 to a patient record in the electronic health record system 304. In this case, the server 310 turns a patient record identifier and some additional basic organizational information to the patient device 308. The patient device 308 transmits to server 310 the client token together with patient identifier and some basic device information (such as the manufacturer, device model number, operating system, and operating system version). In other embodiments, the device may transmit other location-aware information to confirm its location including OPS coordinates or WIFI signal information. After receiving this information, the server 310 requests the electronic health record to create a unique server token to associate with future transmissions from the patient device 308. Like the client token, the server token is a unique key, for example a unique, base64 encoded key. The server token asks as a shared secreted between the patient device 308 and the electronic health record system 304 that identifies the patient record at the organization. The server 310 then returns the server token to the patient device 308 along path 360. In addition, if the system 300 permits more than the patient as an authorized user of the patient device, the server 310 may also transmit a list of all the authorized user identities with the server token.

It will be appreciated that while this process has been described as two potential steps, an implementation of the back-and-forth communication between the patient device 308 and the server 310 may be handled in a single step or in more than two steps.

Once the patient device 308 has the server token, the secure application on patient device 308 can access the features and functionalities enabled for the particular patient record. In the example embodiment, communication between the patient device 308 and the electronic health record system 304 will use the client and/or server tokens. Accordingly, it will be appreciated that disabling the client token at the electronic health record system 304 will disable the patient device 308 from continuing the access the electronic health record system 304.

Also shown in FIG. 3 is an exemplary unauthorized device 312. Even if unauthorized device finds a copy of the printed computer-readable authentication code 306 (such as if it was disposed of in the trash or recycling bin), if the device 312 tried to authenticate against server 310 with the client token, server 310 would reject the request since the token had been consumed already by patient device 301. Similarly, any attempt by device 312 to communicate with the electronic health record system 304 using only the client token would fail since it would not have the server token. The system 300 may implement other security level checking including comparing the device information of the provisioned device with the device information of the unauthorized device 312.

It should be fully appreciated that while this specification refers to a specific example of using the provisioning system in the context of a patient controlled device with access to patient functionality, it should be readily apparent to one of ordinary skill in the art that this provisioning system can be used in a wide range of application, including access to clinical functionality for providers. Similarly, it can be useful where you bring your own devices are common or where a group of individuals share a fleet of devices. Accordingly, the scope of the invention should be determined from the following claims and not limited by the above disclosure.

We claim:

1. A method for securely provisioning access to an electronic health record system implemented using a computer server to a mobile device, the method comprising the steps of:

a) reading, at the mobile device, a computer-readable authentication code, the computer-readable authentication code comprising a unique client token generated by the electronic health record system;

b) transmitting, from the mobile device to the electronic health record system, a request for provisioning the mobile device to the electronic health record system, the request including the unique client token comprising device identification information uniquely identifying the physical mobile device that read the computer-readable authentication code;

c) receiving a provisioning notification, from the electronic health record system at the mobile device, the provisioning notification including a unique server token generated in response to and based on the received device identification information so as to be specific to the physical mobile device, the unique server token identifying a patient record in the electronic health record system;

d) transmitting, from the mobile device to the electronic health record, a request for patient information stored in the electronic health record system, the request including the unique client token and the unique server token; and e) receiving at the mobile device the patient information requested based on a verification of prior provisioning, the unique client token and the unique server token.

2. The method of claim 1, wherein the computer-readable authentication code is a 2D barcode.

3. The method of claim 2, wherein the computer-readable authentication code further comprises a server address of the electronic health record system.

4. The method of claim 1, wherein the computer-readable authentication code expires after a period of time.

5. The method of claim 1, wherein the computer-readable authentication code can be used only once.

6. The method of claim 1, wherein the step of transmitting a request for provisioning transmitting the unique client token further comprises transmitting device information including at least one of the device manufacturer, a device identifier specific to the physical device, a patient identifier associated with the device, and device location information.

* * * * *